(12) United States Patent
Park et al.

(10) Patent No.: US 10,034,815 B2
(45) Date of Patent: Jul. 31, 2018

(54) VIBRATING STIMULUS PAD

(71) Applicant: AMOREPACIFIC CORPORATION, Seoul (KR)

(72) Inventors: Changman Park, Seoul (KR); Sungwon Yi, Seoul (KR); Changkeun Lee, Seoul (KR); Kwanghyun Shin, Seoul (KR); Taehong Shin, Seoul (KR); Seunghwan Yi, Seoul (KR); Taekjin Oh, Seoul (KR); Byungyoung Kang, Seoul (KR)

(73) Assignee: AMOREPACIFIC CORPORATION, Seoul (KR)

( * ) Notice: Subject to any disclaimer, the term of this patent is extended or adjusted under 35 U.S.C. 154(b) by 1109 days.

(21) Appl. No.: 14/358,035

(22) PCT Filed: Nov. 13, 2012

(86) PCT No.: PCT/KR2012/009533
§ 371 (c)(1),
(2) Date: May 13, 2014

(87) PCT Pub. No.: WO2013/073808
PCT Pub. Date: May 23, 2013

(65) Prior Publication Data
US 2014/0309563 A1 Oct. 16, 2014

(30) Foreign Application Priority Data
Nov. 17, 2011 (KR) .................. 20-2011-0010216 U

(51) Int. Cl.
*A61H 23/02* (2006.01)
*A61N 1/30* (2006.01)
(Continued)

(52) U.S. Cl.
CPC ............... *A61H 23/02* (2013.01); *A61F 7/02* (2013.01); *A61F 7/034* (2013.01); *A61N 1/0492* (2013.01);
(Continued)

(58) Field of Classification Search
CPC ................... A61H 23/02; A61H 39/06; A61H 2201/0207; A61H 2201/0278;
(Continued)

(56) References Cited

U.S. PATENT DOCUMENTS

2006/0276741 A1* 12/2006 Henley .................. A61N 1/044
604/20
2007/0100317 A1* 5/2007 Fischer .................. A61N 1/044
604/501

(Continued)

FOREIGN PATENT DOCUMENTS

KR 20-0167444 Y1 2/2000
KR 20-0219490 Y1 4/2001
(Continued)

OTHER PUBLICATIONS

International Search Report of PCT/KR2012/009533 dated Mar. 12, 2013.

*Primary Examiner* — Justine Yu
*Assistant Examiner* — Douglas Sul
(74) *Attorney, Agent, or Firm* — Heedong Chae; Lucern, PC

(57) ABSTRACT

The present invention includes a flexible main body; a drug layer attached to a bottom surface of the main body and formed of an additive mixed with a drug and formed of anti-inflammatory analgesic drugs; a vibrating module attached on a top surface of the main body and including a vibration motor and a battery; and a plurality of legs installed along the perimeter of the main body and being (Continued)

adhesive. Through this configuration in which the main body is formed of a flexible material, and the plurality of legs are adhesive and are attached along the perimeter of the main body, the vibrating stimulus pad may be easily attached on an unwell body region to which attachment is difficult such as a joint region.

5 Claims, 4 Drawing Sheets

(51) Int. Cl.
*A61F 7/02* (2006.01)
*A61F 7/03* (2006.01)
*A61N 1/32* (2006.01)
*A61K 9/70* (2006.01)
*A61N 1/04* (2006.01)

(52) U.S. Cl.
CPC ........ *A61H 2201/0207* (2013.01); *A61H 2201/0228* (2013.01); *A61H 2201/165* (2013.01); *A61K 9/7038* (2013.01); *A61N 1/0408* (2013.01); *A61N 1/0472* (2013.01); *A61N 1/32* (2013.01)

(58) Field of Classification Search
CPC ........ A61H 2201/105; A61H 2201/165; A61N 1/0472; A61N 1/322; A61N 1/325; A61N 1/0412; A61N 1/042; A61N 1/0424; A61N 1/0428; A61N 1/044; A61N 1/32
USPC ............ 602/41, 52, 54, 55, 56, 78, 79
See application file for complete search history.

(56) References Cited

U.S. PATENT DOCUMENTS

| | | | |
|---|---|---|---|
| 2007/0260171 A1* | 11/2007 | Higuchi | A61N 1/044 604/20 |
| 2009/0171313 A1* | 7/2009 | Yamamoto | A61N 1/044 604/501 |
| 2009/0299266 A1* | 12/2009 | Bernabei | A61H 23/0263 604/20 |
| 2010/0331810 A1* | 12/2010 | Imran | A61N 1/044 604/501 |
| 2011/0264028 A1* | 10/2011 | Ramdas | A61M 5/14248 604/20 |

FOREIGN PATENT DOCUMENTS

| | | |
|---|---|---|
| KR | 10-2007-0079760 A | 8/2007 |
| KR | 10-2011-0011789 A | 2/2011 |

* cited by examiner

-- Prior Art --

VIBRATING STIMULUS PAD

CROSS-REFERENCE TO RELATED APPLICATIONS

This application is the National Stage of International Application No. PCT/KR/2012/09533, filed Nov. 13, 2012, which claims benefit of foreign priority of Korean Patent Application No. 10-2011-0010216, filed Nov. 17, 2011, which is incorporated by reference in its entirety into this application.

FIELD OF THE INVENTION

The present invention relates to a vibrating stimulus pad, and particularly to a vibrating stimulus pad being capable to be easily attached to an affected part of a body, such as a joint, to which the pad is generally difficult to be well attached.

DESCRIPTION OF THE PRIOR ART

In general, various types of cataplasms (including various patches and puffs) are known as pads attached to affected parts of a patient and comprise anti-inflammatory and/or analgesic drugs. The cataplasmas may be provided by coating one surface of a backing layer having an approximately rectangular shape with adhesives comprising medicine and by attaching a release paper (a protection layer) to the adhesive.

The cataplasma is used in a manner that when the whole pad is attached to an affected part using the adhesive force of the adhesive, after separation of the release paper attached to the adhesive, the medicine contained in the adhesive permeates into the skin of a patient.

However, different from oral administration, injection or direct application of a medicine, since the medicine contained in the adhesive of the cataplasma is absorbed through the skin, it was not easy for a medicine to be absorbed and/or to be permeated deep enough through the patients skin.

Moreover, since the conventional cataplasmas are mainly manufactured to mitigate arthralgia or myalgia and are directly attached to an affected part, they do not suit the purposes to treat internal symptoms or pains, and their functions and uses have to be maintained simple.

For these reasons, technical efforts to increase permeation of medicine into an affected part have been carried out and an invention of improved permeation of medicine by generating vibration is disdosed herein as part of these technical efforts.

FIG. 1 is a view illustrating an example of a conventional vibrating stimulus pad. As illustrated, the conventional vibrating stimulus pad 10 includes a pad 11, a control unit 12, a power supply 13, a vibration generator 14, a magnetic force generator 15, a cover 16, a release paper 17, and a nonwoven fabric 18. The control unit 12, the power supply 13, and the vibration generator 14 are installed on one surface of the pad 11 while they are connected to each other, and the magnetic force generator 15 made of a magnet and a far infrared ray generating material 19 of grains are attached on the surface. The cover 16 is attached to the pad 11 to cover the control unit 12, the power supply 13, and the vibration generator 14, and the release paper 17 is attached on the other surface of the pad 11. Finally, the nonwoven fabric 18 is attached to a surface of the pad 11 to cover the whole surface of the pad 11.

However, the conventional vibrating stimulus pad has the same appearance and the same attaching function onto an affected part as those of a conventional pad without a vibration function, and thus has the same drawbacks as that of the conventional pad, i.e. difficulty to be attached to a human joint.

That is, the conventional vibrating stimulus pad has an attaching force onto a human affected part completely depending on the adhesive force of the adhesive layer. But a human joint has not only more than one parts through which the joint is bending ("a bending part") but also the bending part(s) frequently moves along with the human body activities. Thus, a part of the conventional vibrating stimulus pad gets to be separated from the affected part around the bending part of the joint. Then, the separated part of the conventional vibrating stimulus pad gets gradually dry due to the exposure of the adhesive layer to the air and the adhesive force is deteriorated as time goes by, thereby resulting in detachment of the pad from the affected part.

Therefore, an improved vibrating stimulus pad has been required to be developed that it can be well attached to an affected part, such as a joint to which the pad is generally difficult to be attached.

Moreover, since the conventional vibrating stimulus pad provides no other function than permeating medicine into an affected part by vibration, its functions have been very limited.

DETAILED DESCRIPTION OF THE INVENTION

Technical Problem

Accordingly, the present invention has been made to solve the above-mentioned problems presented in the prior art, and an object of the present invention is to provide a vibrating stimulus pad easily attached to a affected part to which the pad is difficult to be attached.

The present also provides a vibrating stimulus pad to be able to carrying out physical therapy through vibrating stimulus by applying vibration to an affected part of the body and simultaneously to maximize permeation of medicine into the affected part.

The present invention further provides a vibrating stimulus pad for soothing the affected part and for mitigating a pain by applying warmth or low frequency stimulus to the affected part.

Technical Solution

In order to solve the problems described above, there is provided a vibrating stimulus pad comprising a flexible body; a drug layer attached to a lower surface of the body and comprising adhesive in which anti-inflammatory and/or analgesic drugs are contained; a vibration module attached to an upper surface of the body and comprising a vibration motor and a battery; and a plurality of adhesive legs installed along the circumference of the body.

Each of the adhesive legs comprises an adhesive sucker and a flexible connector extending from the body to connect the sucker to the body, wherein the connectors have an arc-shape bent toward the upper surface of the body to transmit an elastic force to the body to be able to be tightly attached to an affected part.

Moreover, the plurality of adhesive legs further comprises low frequency electrodes.

The vibrating stimulus pad further comprises an exothermic layer in which an exothermic wire is installed on the upper surface of the body.

Moreover, the exothermic layer and the vibration module are sequentially installed on the upper surface of the body.

Advantageous Effects

According to the present invention, the vibrating stimulus pad may be well attached to an affected part of a patient, to which the pad is difficult to be attached, through a flexible body and a plurality of adhesive legs along the circumference of the body. That is, the plurality of legs are attached to a bending part around a joint and restricts the separation of the vibrating stimulus pad from the affected part to the most as possible.

Furthermore, vibrations are applied to the affected part of human body by the vibration module attached to the body of the pad so that physical therapy is carried out by the vibrating stimulus and simultaneously permeation of medicine contained in the drug layer which is attached to the part facing the affected part of the human body can be maximized.

By applying warmth through the exothermic layer or low frequency stimulus through low frequency electrodes attached to the plurality legs to the affected part, it may be soothed and a pain may be mitigated. Hence physical therapy and drug treatment can be carried out simultaneously due to a vibration module, an exothermic layer, the low frequency electrodes, and drug layer containing various western medicines and/or oriental medicines.

DETAILED DESCRIPTION OF THE PREFERRED EMBODIMENTS

Hereinafter, embodiments of the present invention will be described in detail with reference to the accompanying drawings.

Figure 1:
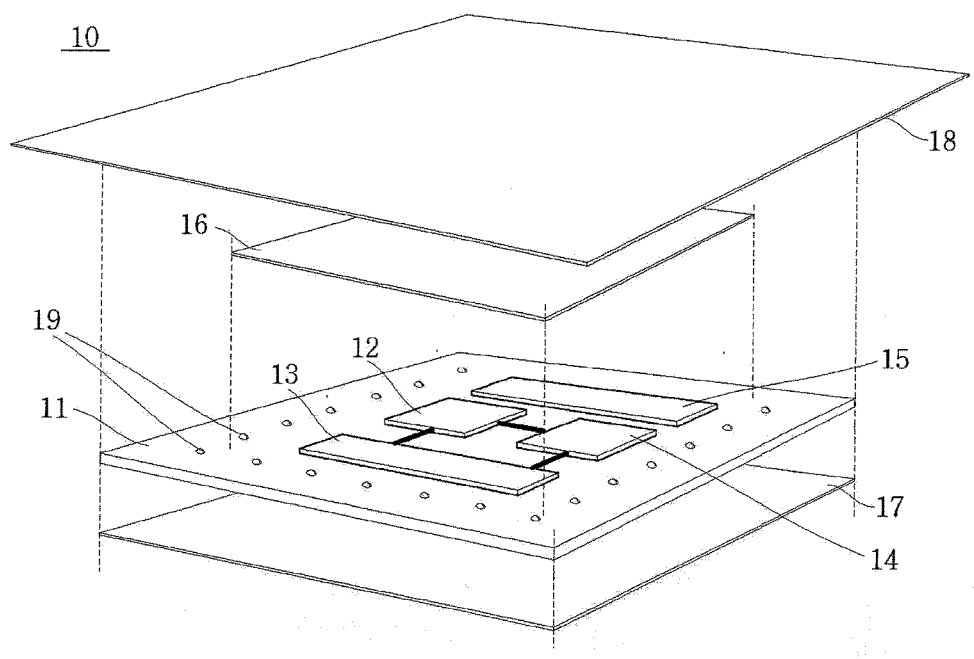
FIG. 1 is a view illustrating a conventional vibrating stimulus pad.
Figure 2:
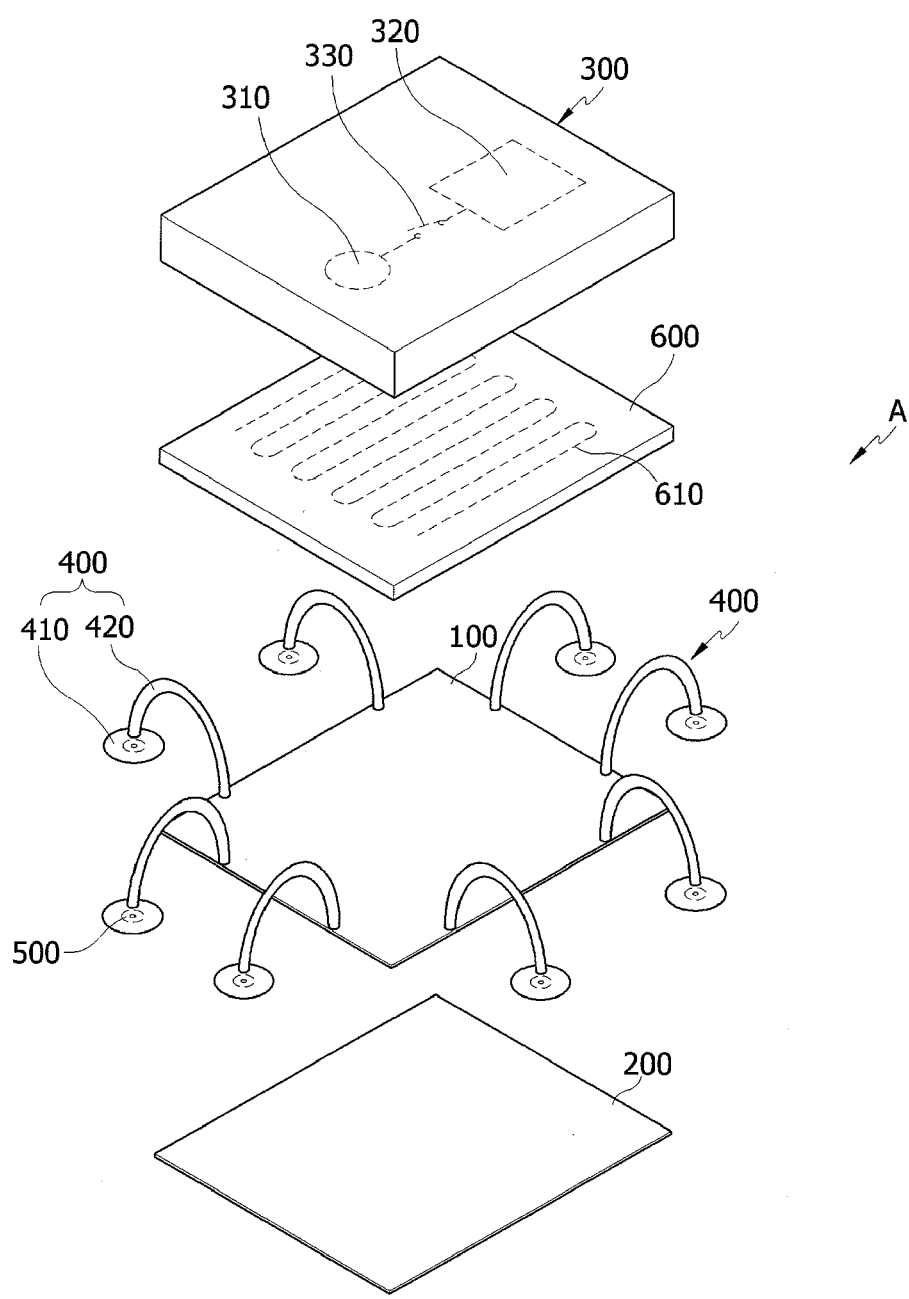
FIG. 2 is an exploded perspective view illustrating a vibrating stimulus pad according to an embodiment of the present invention.
Figure 3:
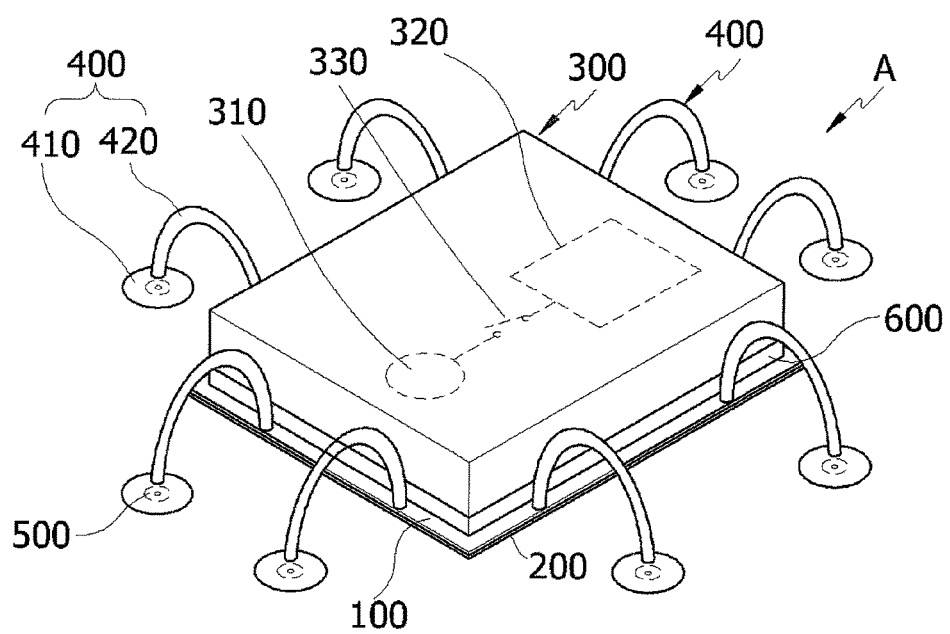
FIG. 3 is a perspective view illustrating an assembly of the vibrating stimulus pad in FIG. 2.
Figure 4:
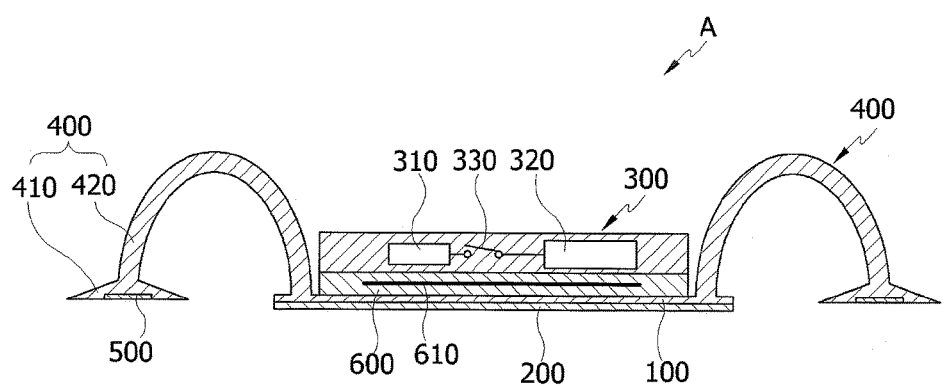
FIG. 4 is a sectional view of FIG. 3.

FIG. 2 is an exploded perspective view illustrating a vibrating stimulus pad according to an embodiment of the present invention. FIG. 3 is a perspective view illustrating an assembly of the vibrating stimulus pad in FIG. 2. FIG. 4 is a sectional view of FIG. 3.

As illustrated in FIGS. 2 to 4, a vibrating stimulus pad A according to an embodiment of the present invention comprises a flexible body 100, a drug layer 200 attached to a lower surface of the body 100, that is, to a portion facing a patients affected part and comprising adhesive in which anti-inflammatory and/or analgesic drugs are contained, and a vibration module 300 attached to an upper surface of the body 100 and having a vibration motor 310 and a battery 320.

First, the body 100 is made of a flexible plastic, silicon, and the like and has a rectangular shape.

Moreover, a plurality of legs 400 with adhesive forces extends along the circumference of the body 100.

In this case, the number of legs 400 is preferably six to eight and is equally spaced from each other along the circumference of the body 100. However, it is noted that the number of the legs 400 may be increased or decreased as necessary.

Each of the legs 400 comprises a sucker 410 with an adhesive force and a flexible connector 420 extending from the body 100 to connect the body 100 to the sucker 410. The connector 420 has an arc-shape bending toward the body 100 so that the connectors 420 apply elastic forces to the body such that the body 100 is attached tightly to a patients affected part of the body, while the connectors 420 are fixed to the affected part by the suckers 410.

The legs 400 extend from the body 100 and are made of the same material as that of the body 100. However, in the case where the connector 420 is made of a flexible material and a fixing force of the body 100 is not strong enough, the legs 400 may be made of other material having higher elastic forces than that of the body 100.

Thus, due to the body 100 made of a flexible material and the plurality of legs 400 attached to the circumference of the body 100 and added with adhesive forces, the vibrating stimulus pad 100 may be easily attached to a patient's affected part such as a joint to which a pad is difficult to be attached.

That is, the plurality of legs 400 is attached to parts bent along a joint, and restricts the vibrating stimulus pad A from being separated from the patients affected part to the most as possible.

The plurality of legs 400 further comprises low frequency electrodes 500 which are preferably provided in the suckers 410. The low frequency electrodes 500 are powered through the battery 320 of the vibration module 300.

Moreover, preferably the body 100 or the vibration module 200 further comprises electronic oscillators (not shown) which generate a low frequency current with the electric power applied from the battery 320 and provide the generated low frequency current to the low frequency electrodes 500.

The body 100 further comprises an exothermic layer 600 in which an exothermic wire 610 is equipped, while the exothermic layer 600 is powered from the battery 320 of the vibration module 300.

The vibrating stimulus pad A further comprises a power switch 330 electrically connected to the battery 320 to control the power supply, wherein the electric power is supplied to the vibration module 300, the low frequency electrodes 500, and the exothermic layer 600 when the power switch 330 is switched "ON."

The exothermic layer 600 and the vibration module 300 are sequentially installed on the upper surface of the body 100.

As seen from the embodiments of FIGS. 2 to 4, the vibrating stimulus pad A of the present invention carries out physical therapy using vibrating stimulus by applying vibration to a patients affected part by the vibration module 300 which is attached to the body 100 and maximizes permeation of medicine contained in the drug layer 200 that is attached to a portion of the body 100 which will face the patient affected part.

Moreover, warmth or the low frequency stimulus is applied to the patients affected part through the exothermic layer 600 and the low frequency electrodes 500 attached to the plurality of legs 400, so that the patients affected part can be soothed and pain can be mitigated. Thus, the vibration module 300, the exothermic layer 600, the low frequency electrodes 500, and the drug layer 200 containing various western and/or oriental medicines enable physical therapy and drug treatment at the same time.

The thickness of the vibrating stimulus pad A in FIGS. 2 to 4 is illustrated with exaggeration for understanding and explaining the internal structure of the pad according to the present invention, and it is noted herewith that the actual product is manufactured to be thinner than that shown in the drawings.

Although a preferred embodiment of the present invention has been described for illustrative purposes, those skilled in the art will appreciate that various modifications, additions and substitutions are possible, without departing from the scope and spirit of the invention as disclosed in the accompanying claims.

DESCRIPTION OF REFERENCE NUMERALS

A: vibrating stimulus pad 100: body
200: drug layer 300: vibration module
400: leg 500: low frequency electrode
600: exothermic layer

The invention claimed is:

1. A vibrating stimulus pad comprising:
a flexible body;
a drug layer attached to a lower surface of the body and made of adhesive in which anti-inflammatory and/or analgesic drugs are contained;
a vibration module attached to an upper surface of the body and including a vibration motor and a battery; and
a plurality of adhesive legs,
wherein the body has an outer edge which is not attached to the vibration module,
wherein the plurality of adhesive legs are attached to an upper surface of the outer edge of the body,
wherein each of the adhesive legs comprises an adhesive sucker and a flexible connector, and
wherein the connectors are longitudinally constructed in an arc-shape which extends upwardly from the upper surface of the outer edge of the body downwardly to the sucker such that the connectors exert tensile force to the upper surface of the outer edge of the body in order for the body and the outer edge of the body to be securely attached to a patient's affected part when the adhesive suckers are attached to the patient.

2. The vibrating stimulus pad of claim 1, wherein the plurality of adhesive legs further comprises electrodes.

3. The vibrating stimulus pad of claim 1, further comprising an exothermic layer in which an exothermic wire is installed in the upper surface of the body.

4. The vibrating stimulus pad of claim 3, wherein the exothermic layer and the vibration module are sequentially installed on the upper surface of the body.

5. The vibrating stimulus pad of claim 1, the connectors are made of material having a elasticity greater than that of material for the body.

* * * * *